United States Patent [19]

Petruzzi

[11] Patent Number: 4,474,174

[45] Date of Patent: Oct. 2, 1984

[54] SURGICAL INSTRUMENT FOR AN ENDOSCOPE

[75] Inventor: Claude E. Petruzzi, Bronxville, N.Y.

[73] Assignee: American Hospital Supply Corp., Evanston, Ill.

[21] Appl. No.: 469,031

[22] Filed: Feb. 23, 1983

Related U.S. Application Data

[63] Continuation of Ser. No. 208,805, Nov. 20, 1980, abandoned, which is a continuation of Ser. No. 040,771, May 21, 1979, abandoned.

[51] Int. Cl.³ .................. A61B 17/36; A61B 17/32
[52] U.S. Cl. .................. 128/4; 128/303.15; 128/772; 604/95
[58] Field of Search .................. 128/3–8, 128/749–759, 303.14, 303.15, 303.17, 784–786, 772, 656–658, 356; 64/2 R, 3, 4; 604/93, 95, 118

[56] References Cited

U.S. PATENT DOCUMENTS

| | | | |
|---|---|---|---|
| 2,022,065 | 11/1935 | Wappler | 128/786 |
| 2,047,535 | 7/1936 | Wappler | 128/4 X |
| 2,118,631 | 5/1938 | Wappler | 128/657 X |
| 2,821,092 | 1/1958 | Cordora et al. | 64/2 X |
| 2,828,747 | 4/1958 | August | 128/303.14 |
| 3,731,671 | 5/1973 | Mageoh | 128/772 |
| 3,858,586 | 1/1975 | Lessen | 128/4 X |
| 3,897,775 | 8/1975 | Furihata | 128/6 |
| 4,030,503 | 6/1977 | Clark | 128/356 X |
| 4,033,331 | 7/1977 | Guss et al. | 128/657 |
| 4,054,127 | 10/1977 | Milan et al. | 128/757 |
| 4,108,162 | 8/1978 | Chikashige et al. | 128/756 |
| 4,200,111 | 4/1980 | Harris | 128/751 |
| 4,257,421 | 3/1981 | Beal | 128/657 |

FOREIGN PATENT DOCUMENTS

| | | | |
|---|---|---|---|
| 480520 | 8/1929 | Fed. Rep. of Germany | 128/7 |
| 636912 | 4/1928 | France | 128/6 |

*Primary Examiner*—Michael H. Thaler
*Attorney, Agent, or Firm*—Perman & Green

[57] ABSTRACT

A surgical instrument is described for use with a flexible endoscope. The instrument includes a tubular member such as a catheter, in which a surgical tool is placed. The tool is formed of a working end and a control wire connected thereto and formed of a helically twisted flat ribbon sized to slidingly fit within the lumen of the tubular member. With a helically twisted control wire, the instrument may be bent and flexed in any plane without breakage, yet preserving accurate axial positional control substantially without longitudinal backlash. A distal end of the tubular member has a predetermined bend, with a channel cut therein in a manner selected to enable the working end of the tool, such as a knife, to be automatically moved into the channel and thus reliably extended from a side of the distal end of the catheter. A manipulator is used at the proximal end of the endoscope to precisely control the position of the working end of the surgical tool.

19 Claims, 13 Drawing Figures

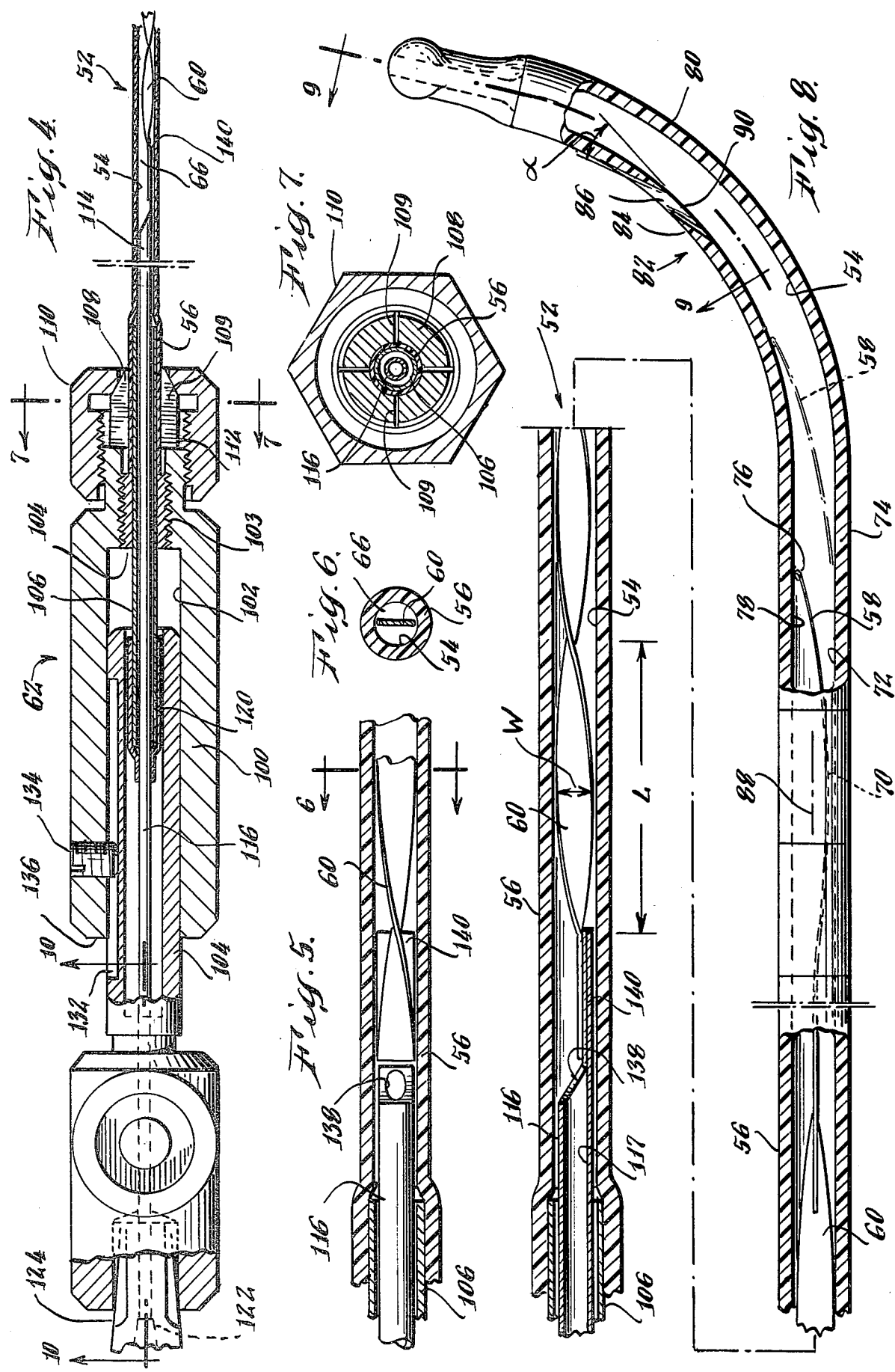

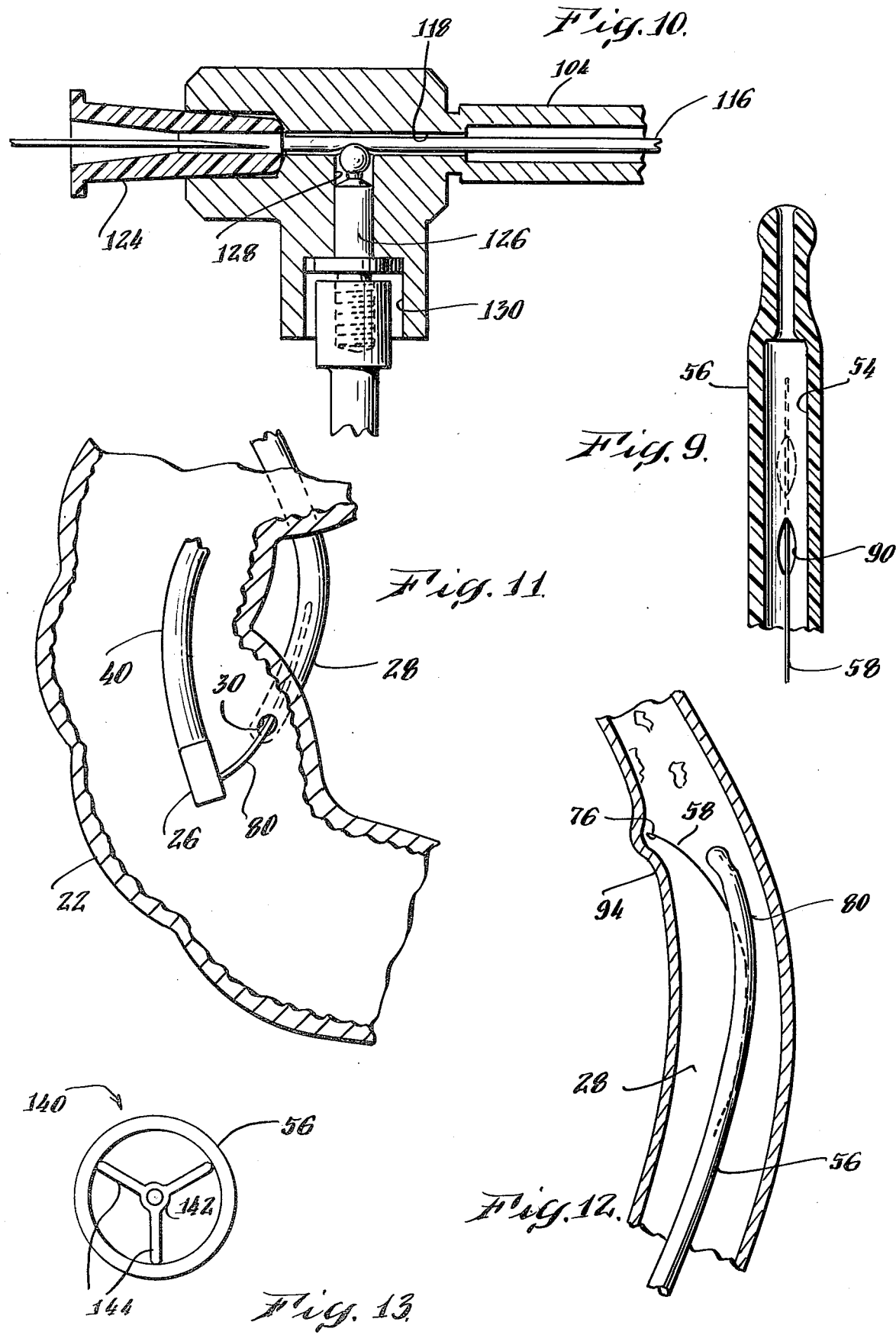

SURGICAL INSTRUMENT FOR AN ENDOSCOPE

This is a continuation of application Ser. No. 06/208,805 filed Nov. 20, 1980, abandoned, which, in turn, is a continuation of application Ser. No. 040,771 filed on May 21, 1979, abandoned.

FIELD OF THE INVENTION

This invention relates to an accessory for an endoscope. More specifically, this invention relates to a surgical instrument for use with a flexible endoscope such as a duodenoscope.

BACKGROUND OF THE INVENTION

Flexible endoscopes are well known and commonly are provided with a flexible shaft capable of being advanced past corners to investigate deep body cavities. An endoscope commonly has a fiber optic light carrier and viewer whereby a physician may inspect the body cavity. The fiber optics is flexible and is located in a duct of the flexible shaft to terminate with suitable viewing optics at a distal tip of the shaft. Other endoscope tubular ducts are provided through which, for example, a liquid can be passed such as water and a surgical tool may be employed to conduct a surgical procedure under view with the aid of the flexible fiber optics.

The surgical tools available for use through an endoscope duct vary depending upon the particular procedure being used or the physiological problem being investigated. In one tool, for example, a measuring device is provided, which is straight as it is passed through an endoscope duct, but when it emerges at the tip resumes a particular shape adapted to, for example, measure tumors with the aid of visible graduations.

In another surgical tool a conductive snare is located at the end of a long line and inserted in a long catheter. The snare is controlled with a handle at a proximal end of the endoscope from where the snare's protrusion at the distal end of the catheter and electrical cutting action is controlled. Other surgical tools may be forceps, scissors, needles, brushes with various shapes adapted often for a particular purpose.

For example, one type of surgical tool known as a papillotome is designed to perform a complex surgical procedure involving an investigation of the duodenum, the portion of the alimentary canal immediately downstream of the stomach and a radiographic investigation of the billiary or common duct leading to the pancreas and gall bladder. The common duct terminates in a valve, the ampulla of Vater, or papilla.

If the investigation indicates the presence of stones in the common duct, the condition may be relieved by opening an orifice into the duodenum wall portion which is common with the common duct to let the stones escape. This orifice can be made by cutting with high frequency techniques.

In practice, a duodenoscope is maneuvered until the ampulla of Vater is observed. A catheter is extended from the distal tip and manipulated into the common duct. Once the catheter is inside, a radio-opaque material is fed through the catheter to investigate the duct for obstructions or growths with a radiogram.

In many cases the observation of an obstruction such as a gall stone can be immediately treated by use of an electric or high frequency knife integrally associated with the catheter whose distal end is now inside the common duct. The cutting action usually proceeds from a blind or invisible position of the catheter as it is advanced or withdrawn from the common duct, to thus open the wall between the common duct and the duodenum and enable the discharge of blocking materials.

With one such catheter knife a wire is used inside the catheter lumen and is passed through a side opening near the distal catheter end to lie externally along the end portion of the catheter to its tip to which the wire is anchored. When the wire is retracted, it forms a chord and as the wire is electrified, cuts a slit. A disadvantage of this type of papillotomy knife, or electrode as it may also be called, is that the length of the cut depends upon the length of the chord, which in turn changes with different chord tensions. Since the chord tension changes rapidly as a cut is made, precise control over the length of the cut is difficult at best and more so when one considers the backlash involved in the retraction and extension of the wire.

In another catheter knife an end portion of an electric wire is passed outside of the catheter lumen for a small distance to an anchor point located a short distance from the catheter distal tip. A knife is formed by advancing the wire into the lumen thus forming a hump of the end portion. This type of knife provides poor control with danger to adjacent structures during cutting.

SUMMARY OF THE INVENTION

With a surgical instrument for a flexible endoscope in accordance with the invention, improved control over the position of a surgical tool inside a catheter is obtained with a substantial reduction of backlash. As a result, the retraction and extension of the tool at the distal tip of the endoscope can be precisely measured at the proximal end of the endoscope.

This improvement in control is achieved by employing, within the lumen of a hollow channel, a surgical tool formed of a distal working end and a longitudinal control wire connected thereto. The control wire is provided with a lumen wall contacting support sized to radially stabilize the position of the control wire inside the lumen while providing sliding contact with the lumen wall so that the surgical tool can be accurately retracted and extended from the proximal end of the flexible endoscope.

As described herein for one embodiment for a surgical instrument in accordance with the invention, the control wire is formed of a longitudinal conductive flat ribbon which is helically twisted over its length. The width of the ribbon corresponds to the inside diameter of a tubular channel or lumen so as to allow sliding movemeint while minimizing radial displacement of the ribbon inside the lumen. The ribbon thickness is preferably thin relative to the inner diameter of the lumen so as to provide a passageway through the lumen sufficient to inject a fluid such as a gas or liquid for use at the distal end. The ribbon cross-section preferably is not greater than about one half of the cross-sectional area of the lumen.

The ribbon shaped control wire has strength and rigidity required for durability when deflected about an axis perpendicular to the thin side and flexibility required to bend on a desired radius when deflected about an axis perpendicular to the large flat side. By twisting the control wire ribbon into a spiral, both strength and flexibility are available when bent in any given plane. The spiral further permits a free flow of liquid as it passes through the containing tube and the rectangular cross-section being substantially less than that of the containing tube enhances liquid flow rate.

With a surgical tool in accordance with the invention, a procedure such as described for the removal of gall stones by cutting of the wall between the duodenum and the common duct can be carried out with greater precision and safety to the patient.

Such procedure is particularly improved by employing a surgical instrument in accordance with the invention, having a working end in the form of an electric wire with a predisposed curvature and located inside the lumen of an insulative flexible catheter. The catheter has a straightenable, normally bent working segment at a distal end which, when unrestrained, forms a bend with a preferential orientation. The bend is provided with a channel extending through the wall on the inside curve of the bend from an opening to the catheter lumen, with the channel inclined at an angle relative to the catheter axis so that the electric wire is automatically guided into the channel as a result of the preferential orientation of the catheter working segment. With a surgical instrument in accordance with the invention, the retraction, extension and proximal control over the instrument is advantageously enhanced.

It is, therefore, an object of the invention to provide a surgical instrument for use in a flexible endoscope and with which instrument an enhanced control is obtained. It is a further object of the invention to provide an improved surgical instrument for performing a papillotomy procedure. It is still another object of the invention to provide an improved catheter and a surgical tool for use with a flexible endoscope.

These and other objects and advantages of the invention can be understood from the following description of several embodiments of the invention as described in conjunction with the following drawings.

BRIEF DESCRIPTION OF DRAWINGS

FIG. 4 is a section view of the manipulator used with a surgical instrument in accordance with the invention;

FIG. 5 is an enlarged partial section view of the connection made between the surgical tool in accordance with the invention and the manipulator as illustrated in FIG. 4;

FIG. 6 is a section view taken along line 6—6 in FIG. 5;

FIG. 7 is a section view of the manipulator taken along the line 7—7 of FIG. 4;

FIG. 8 is an enlarged side sectional view of a portion of the surgical instrument in accordance with the invention;

FIG. 9 is a section view taken along line 9—9 in FIG. 8 of the distal end of a catheter used with the surgical instrument in accordance with the invention;

FIG. 10 is a section view taken along the line 10—10 in FIG. 4 of a coupling employed with the manipulator of FIG. 4;

FIG. 11 is an enlarged section view of the distal tip of the flexible endoscope with the distal end of the surgical instrument maneuvered into the common duct leading to the duodenum;

FIG. 12 is an enlarged section view of the distal end of the surgical instrument inside the common duct; and FIG. 13 is an enlarged section view of another form for a control wire in accordance with the invention.

DETAILED DESCRIPTION OF DRAWINGS

Figure 1:
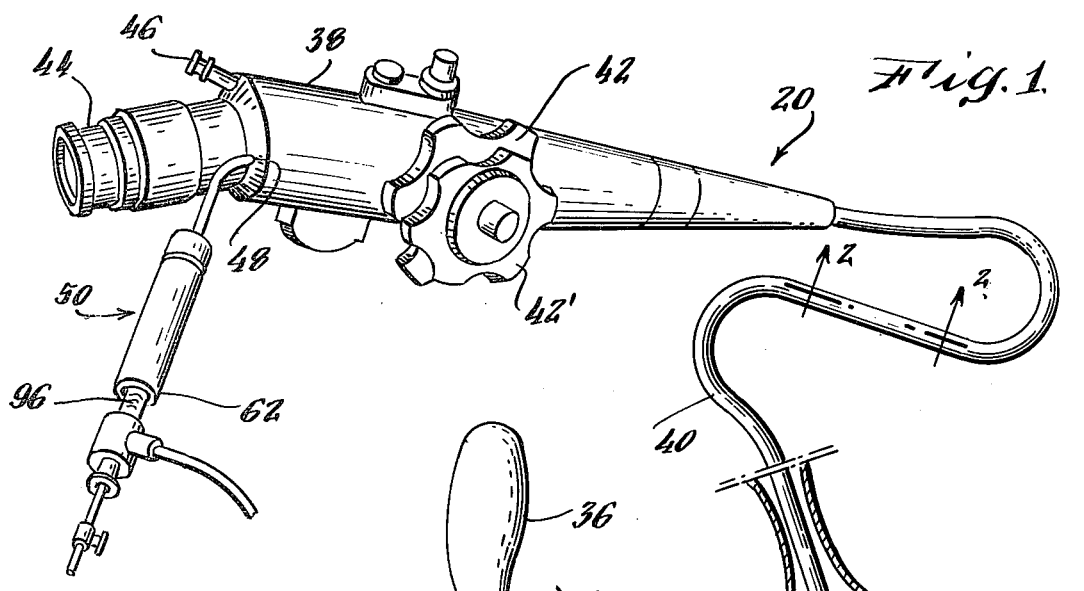
FIG. 1 is a partial perspective and section view of a flexible endoscope employing a surgical instrument in accordance with the invention.

With reference to FIG. 1, a conventional flexible endoscope 20 is shown, such as a duodenoscope, which has been maneuvered into a position for investigating the duodenum 22 below a stomach 24. The distal tip 26 of the endoscope 20 is positioned to inspect the common duct 28 behind a valve 30 known as the ampulla of Vater. The common duct 28 leads to the pancreas duct 32 and the cystic duct 34 connected to the gall bladder 36.

The flexible endoscope 20 is formed of a proximal head 38 and flexible shaft 40. The head 38 has control wheels 42—42' which control the orientation of distal tip 26 to enable the physician to advance the flexible shaft 40 into deep body cavities. The proximal head 38 includes an eyepiece 44, a water supply entry port 46 and an entry port 48 to receive a surgical instrument such as 50. The endoscope 20 is of well known design and thus is provided with an optical fiber path (not shown) used to transmit light for the illumination of the body cavity opposite the distal tip 26 and a fiber optic bundle (not shown) to view body cavity images through eye piece 44. The water supply port 46 communicates with a suitable channel inside the flexible shaft 40 to terminate at distal tip 26 for the removal of obstructions or materials lodged over lenses at the distal tip. The surgical instrument 50 is passed through another channel in the flexible shaft to perform procedures.

When a flexible endoscope such as 20 is used to perform a surgical procedure, the need for precise positional control over the distal tip 26 can be appreciated, particularly when a difficult to find common duct 28 needs to be investigated. An even greater positional control is necessary for the application of surgical instruments. When the flexible shaft 40 is maneuvered around corners in the manner as illustrated in FIG. 1, the control over a surgical tool, such as a snare, inside a channel or the lumen of a catheter often is accompanied by backlash caused by the tendency of the control wire leading to the snare to lie along the inside wall of a bend when retracted and along the outside wall of the bend when being extended.

With certain surgical tools a tightly coiled control wire is used whose diameter fills the duct of a flexible shaft or lumen of a catheter and thus remains in a stable radial position during use. With such tool, however, an inadequate space is left within the lumen to provide fluids often needed during the surgical procedure. When a thin walled tubular material is used as the control wire, an additional passage way for fluid can be obtained, but the smallness of the lumen requires such a thin wall for the control segment that it tends to be easily damaged.

Figure 2:
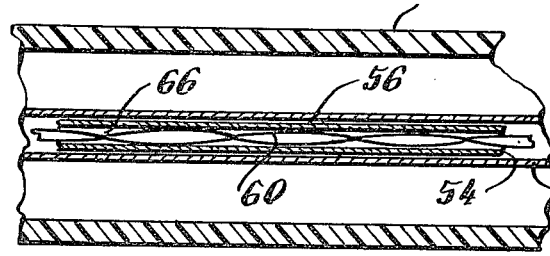
FIG. 2 is an enlarged partial section view of the flexible shaft of the endoscope shown in FIG. 1 and taken along the line 2—2 in FIG. 1.
Figure 3:
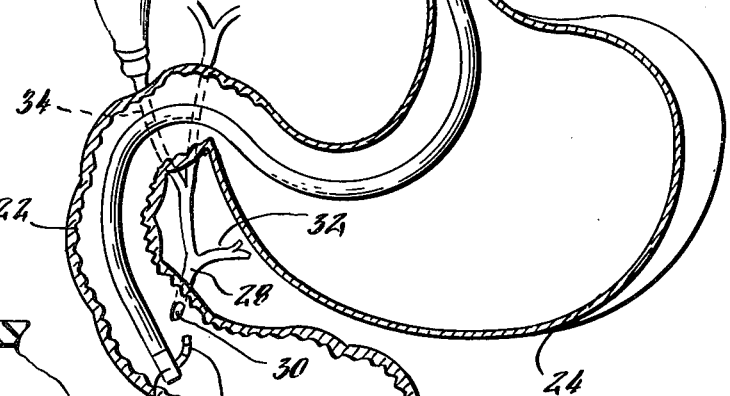
FIG. 3 is an enlarged partial section view of the distal tip of the flexible endoscope shown in FIG. 1.

With reference to FIGS. 2, 3 and 8, a surgical instrument 50 in accordance with the invention is shown using a surgical tool 52 inside the lumen 54 of a catheter 56. Tool 52 includes a working end 58 in the form of a high frequency knife which is connected to a conductive control wire 60, coupled to a manipulator 62 at a proximal end. The catheter 56 is sized to slidingly fit within a duct 64 of the flexible shaft 40. The control wire 60 is shown formed of a flat helically twisted ribbon 60. The ribbon 60 has a width corresponding to the inside diameter of the lumen 54 so that the ribbon 60 has a stabilized radial position. The cross-section of the control wire 60 is sufficiently smaller than the cross-sectional area of the lumen 54 to provide a passageway 66 for fluid from the proximal manipulator 62.

The wire knife 58 as illustrated in FIGS. 3 and 8, has a curvature at its distal end which is sufficient to place a portion 70 of the working end 68 against one side 72 of the catheter wall 74 and thus spring biases a distal tip 76 of knife 58 against side 78 of catheter wall 74. Tip 76 is formed of a closed tight single loop of the wire from which knife 58 is made.

The catheter 56 has a distal working segment 80 which has, when unrestrained, a preferential orientation in the form of a bend 82 as shown in FIGS. 3 and 8. Such bend 82 may be produced with a thermosetting process or the natural tendency of a wound-up coil of the material to bend in this manner may be used. Catheter 56 has sufficient flexibility to straighten inside a duct 64 of flexible shaft 40. The bend 82 has an inside wall 84 along the inside of the bend 82 and a channel 86 is cut therethrough at an angle, α, as measured relative to the lumen axis 88 for a straight form of catheter working segment 80, or as measured relative to a line which is tangential to the channel opening 90 into lumen 54 on the inside wall 84. The channel 86 has, as shown in FIG. 9, a generally longitudinal opening 90, which is so sized that it readily receives tip 76 of surgical knife 58. The size of angle α may vary depending upon the curvature of bend 82. An angle α of about 15° has been found useful.

The preferential orientation of the working segment 80 of catheter 56, the cylindrical internal curvature of lumen 54 and the curvature of the working end 58 of surgical tool 52 within lumen 54 cooperate to maintain end 58 in a predetermined alignment within lumen 54. As a result, tip 76 is automatically guided into channel 86 as the tool 52 is extended by its proximal manipulator 62 towards the working segment 80 of catheter 56. Hence, extension and retraction of the working end 58 of surgical tool 52 can be reliability performed without use of a wedging surface interposed in the lumen 54.

With a surgical instrument 50 in accordance with the invention, a complex surgical procedure such as the investigation and treatment of the common duct can be accurately accomplished. For example as shown in FIG. 11 for one procedure, the flexible shaft 40 is maneuvered such that its distal tip 26 is in a position whereby the catheter 56, with its retracted surgical tool 52, can be inserted into the common duct 28. It may be necessary to tilt the catheter working segment 80 with a wedge 92 (see FIG. 3) to obtain the proper orientation to enter the common duct 28. Control elements for use with wedge 92 are well known.

Once catheter 56 is inside common duct 28, a radio-opaque liquid is supplied through the passageway 66 between the tool 52 and lumen wall 74 and blockages from stones detected. As shown in FIG. 12, the surgical knife 58 may then be extended through channel 86 until tip 76 contacts the duct wall 94 in common between duct 28 and the duodenum 22. The extension of knife 58 can be precisely controlled since backlash is reduced and scale indications such as 96 on manipulator 62 can be relied upon to precisely indicate by how much distance the knife 58 is extended from the catheter channel 86.

A cutting procedure may then be implemented by electrifying the surgical tool 52 and supplying it with the high frequency current. The catheter 56 is formed of an insulative material assuring that electrical energy is applied at the point where tip 76 of knife 58 contacts duct wall 94.

Control over the extension and retraction of surgical instrument 50 is obtained with manipulator 62 which, as more particularly shown in FIG. 4 is formed of outer housing 100 with a through bore 102 within which a control shaft 104 is slidably mounted. Portion 103 of housing bore 102 is threaded to engage an externally threaded sleeve 104 firmly connected to a support tube 106. A distal end of support tube 106 sealingly fits into the proximal end of lumen 54 of catheter 56 which is seated against sleeve 104. A distal end 108 of housing 100 is axially split with four slots 109 to form a clamp when a clamping nut 110 is threaded onto an externally threaded segment 112 of housing 100. Hence, upon use of nut 110, a firm grip is made with catheter 56 while it is also sealingly clamped against support tube 106.

The proximal end of control wire 60 of surgical tool 52 is firmly connected to an extension 114 of a control tube 116 which freely fits within lumen 54 and is sufficiently long to fit with radial clearance through support tube 106 for connection to and in a bore 118 of control shaft 104. A sealing sleeve 120, formed of a heat shrinkable material, is shrunk around the proximal end of support tube 106 and around control tube 116. Sleeve 120 forms a seal with the outer surface of control tube 116.

The proximal end of control tube 116 communicates with a liquid supply port 122 through a conventional Leuer lock 124 penetrated by a needle of a syringe. The control tube thus enables the supply of radio-opaque liquid to the fluid passageway 66.

An electrical connection is made with control tube 116 with a contact 126 (see FIG. 10) applied through a lateral counter bore 128 in control shaft 104. The contact 126 is seated against the bottom of a bore 130. Electrical contact is made with a slight deformation of control tube 116 to thus also firmly retain the latter to control shaft 104.

The extension and extraction of control tube 116 is limited with a slot 132 and a set screw 134 mounted to housing 100 to penetrate bore 102 and a portion of slot 132. The graduations 96, see FIG. 1, may be placed along the sides of slot 132 and measured with reference to the proximal end 136 of housing 100.

The connection between control tube 116 and control wire 60 is so formed as to enable the flow of liquid into passageway 66. Control tube 116 is cut at a slant relative to its longitudinal axis so that the through bore 117 has an enlarged port 138 with passageway 66. A flat extension 140 of control tube 116 is welded to ribbon shaped control wire 60.

With the use of helical twists of the control wire, lateral movement within a lumen is substantially reduced. The number of twists needed to reduce backlash when the instrument is inside a channel of a flexible endoscope depends upon the latter's maximum number of curves and their sharpness. For a highly flexible shaft, a higher number of twists would be desirable though too many twists increases the length of the helical passageway so that fluid flow therethrough is more difficult. In one embodiment for a duodenoscope four twists per inch was found useful though more or less may be used depending upon the particular application.

Preferably the length, L, of a helix or twist is determined with respect to the width of a ribbon shaped control wire. Thus a twist length, L, is preferably made in the range from about four to about fifteen times the width, w, of the ribbon control wire 60.

The cross-sectional size of the ribbon shaped control segment 60 is selected commensurate with structural rigidity while preserving a sufficiently large cross-section for the fluid passageway 66. Since the inside diameter of a catheter lumen 54 tends to be quite small, the cross-sectional area of a ribbon shaped control wire can be made quite small relative to that of lumen 54 without loss of structural integrity. Hence, the cross-sectional area of a ribbon shaped control wire 60 should be preferably no more than about fifty percent of the cross-sectional area of lumen 54 and preferably as small as about twenty-five percent. The cross-sectional area of ribbon control wire 60 may be in the range from about twenty to about sixty percent of that of lumen 54.

For example, a ribbon shaped control wire was used with a ribbon width w of 0.032 inches and a thickness of 0.008 inches to fit inside a catheter lumen having an internal diameter of 0.035 inches. The ribbon was formed with about four twists per inch. The resulting surgical instrument was formed with a catheter made of teflon and having an outside diameter of 0.066 inches and was found suitable for use as a papillotome capable of cutting the ampulla of Vater and the adjoining intramural portion of the billiary or common duct for the removal of entrapped stones.

Having thus described an embodiment for a surgical instrument in accordance with the invention, its advantages can be appreciated. The use of a spiral or twisted rectangular ribbon shaped control wire for the conductor to an electric knife inside a tube eliminates radial motion between the control wire and the tube as the latter is bent. As a result, longitudinal backlash is substantially reduced and any axial motion applied to the control wire is productive in axially moving of the knife.

Another form for a control wire may be used such as 140 depicted in FIG. 13. Control wire 140 is formed of an extruded metal having a central wire portion 142 from which a plurality of at least three sides 144 protrudes radially. The sides are preferably equiangularly spaced and sized to slidingly contact the wall of a tubular channel. The central wire 142 may be hollow and may be helically twisted to obtain the desired flexibility and rigidity.

What is claimed is:

1. A flexible surgical instrument for use in a flexible endoscope wherein the endoscope is a duct extending from a proximal end to a distal end of the endoscope comprising: an elongated flexible catheter sized to enter the proximal end of the endoscope duct and fit therethrough to the distal end of the endoscope duct, the catheter having a lumen surrounded by a lumen wall, the lumen extending from a proximal end of the catheter to a distal end thereof;

a surgical tool sized to slide through a lumen and through an opening in the lumen wall, the tool having a working end and a flexible control wire connected to the working end for manipulation thereof from the proximal end of the catheter, the control wire having a cross-sectional area which is less than the cross-section of the catheter lumen while being shaped to provide a fluid passageway between the control wire and the wall of the lumen, the control wire having a non-cylindrical shape defining at least two lateral edges comprising longitudinally extending continuous support surfaces of narrow transverse extent, the support surfaces being spaced apart from each other a desired amount so that said support surfaces slidingly contact the lumen wall, the support surfaces being arranged to radially stabilize the position of the control wire in and along the catheter lumen when the control wire is placed within the lumen, the control wire having structural rigidity and integrity along its length to insure accurate manipulation of a tip portion of the working end of the surgical tool back and forth through an opening in the lumen, whereby the working end of the surgical tool can be manipulated with reduced longitudinal backlash for an enhancement in the accuracy of the control over the said control wire being in the form of an elongated rectangular ribbon having said lateral edges and having a width sized to enable said support surfaces to slidingly contact the lumen wall, said ribbon being helically twisted to maintain the ribbon radially stabilized within the catheter lumen throughout flectures of the endoscope and provide a continuous fluid passageway and said ribbon has a cross-section area which is less than about one half of the cross-section of the catheter lumen.

2. The flexible surgical instrument as set forth in claim 1 wherein the cross-sectional area of the ribbon shaped control wire is in the range of from about one-quarter to about one-half of the cross-section of the catheter lumen.

3. The flexible surgical instrument as set forth in claim 1 wherein the length of a twist of the ribbon control wire is in the range from about four to about fifteen times the width of the ribbon control wire.

4. A flexible surgical instrument for use in a flexible endoscope wherein the endoscope is a duct extending from a proximal end to a distal end of the endoscope comprising:

an elongated flexible catheter sized to enter the proximal end of the endoscope duct and fit therethrough to the distal end of the endoscope duct, the catheter having a lumen surrounded by a lumen wall, the lumen extending from a proximal end of the catheter to a distal end thereof;

a surgical tool sized to slide through a lumen and through an opening in the lumen wall, the tool having a working end and a flexible control wire connected to the working end for manipulation thereof from the proximal end of the catheter, the control wire having a cross-sectional area which is less than the cross-section of the catheter lumen while being shaped to provide a fluid passageway between the control wire and the wall of the lumen, the control wire having a non-cylindrical shape defining at least two lateral edges comprising longitudinally extending continuous support surfaces of narrow transverse extent, the support surfaces being spaced apart from each other a desired amount so that said support surfaces slidingly contact the lumen wall, the support surfaces being arranged to radially stabilize the position of the control wire in and along the catheter lumen when the control wire is placed within the lumen, the control wire having structural rigidity and integrity along its length to insure accurate manipulation of a tip portion of the working end of the surgical tool back and forth through an opening in the lumen, whereby the working end of the surgical tool can be manipulated with reduced longitudinal backlash for an enhancement in the accuracy of the control over the position of the working end of the tool;

said control wire being in the form of an elongated rectangular ribbon having said lateral edges and having a width sized to enable said support surfaces to slidingly contact the lumen wall, said ribbon being helically twisted to maintain the ribbon radially stabilized within the catheter lumen throughout flectures of the endoscope and provide a continuous fluid passageway.

5. The flexible surgical instrument for use in a flexible endoscope as set forth in claim 4 wherein the control wire is in the form of a longitudinal flexible central wire having a plurality of at least three longitudinal ribs which radially extend from the central wire to slidingly contact the lumen wall.

6. The flexible surgical instrument for use in a flexible endoscope as set forth in claim 5 wherein the central wire is hollow.

7. An instrument for use in a flexible endoscope by insertion into a channel surrounded by a channel wall, comprising:

a surgical tool having a distal working end and a flexible longitudinal control wire connected to the distal working end for the manipulation thereof;

the control wire having a cross sectional area which is less than the cross sectional area of the channel through which the surgical tool is to be inserted, the cross-section being further selectively shaped to enable formation of a fluid passageway external of the control wire upon insertion into the channel, the control wire having a non-cylindrical shape, defining at least two lateral edges comprising longitudinally extending continuous support surfaces of narrow transverse extent, the support surfaces being spaced apart from each other a desired amount so that said support surfaces slidingly contact the channel wall while being retained within the channel with radial positionable stability along the length of the control wire, the control wire having structural rigidity and integrity along its length to assure accurate extension and retraction of the working end of the tool relative to said channel wall whereby the tool, when placed within the channel, may be moved therealong substantially without backlash for improved positional control over the distal working end of the instrument from the proximal end of the endoscope; and the control wire being formed of a longitudinal ribbon of generally rectangular cross section with sides to form said at least two lateral edges, said longitudinal ribbon first being provided along its length with a plurality of twists to form a spiral control wire capable of being flexed in various planes while maintaining said radial positional stability within the channel when the instrument is longitudinally moved within the channel.

8. The instrument as set forth in claim 7 wherein said working end of the surgical tool is flexible with a predetermined curvature, said working end terminating at a tip and having sufficient curvature in the vicinity of the tip so that, when placed within the channel, a portion of the working end near the tip slides against one side of the channel wall and spring biases the tip against another side of the channel wall.

9. The instrument as set forth in claim 8 wherein said working end is a wire provided with said curvature.

10. The instrument as set forth in claim 9 wherein said surgical tool is formed of a conductive material with said working end tip formed into a tight smooth-surfaced loop to form an electric knife.

11. The instrument as set forth in claim 7 further including:

means for longitudinally manipulating the extension and retraction of the working end of the instrument;

a housing having a throudgh bore;

a fluid tube in said housing bore and size to slidingly fit within the channel and connected to the control wire while enabling fluid flow through the tube into said channel;

a support tube mounted to said housing in said bore and sized to fit within the channel while enabling a fluid sealing engagement with the channel wall, said support tube enclosing the fluid tube with radial clearane therebetween;

a slide seal between the support tube and the fluid tube to prevent leakage of fluid through said radial clearance; and coupling means attached to a proximal end of the fluid tube for manipulation thereof and coupling of fluid thereto.

12. A surgical instrument for use with an endoscope to cut tissue under endoscopic control said instrument and endoscope each having a proximal end and a distal end, comprising flexible hollow tubular means having a length commensurate with that needed to extend from the proximal end to the distal end of the endoscope, said tubular means having a lumen of a preselected diameter;

flexible wire means for conducting high frequency current to a distal end of the wire means to the tissue to be cut substantially contained within said tubular means;

manipulator means connected to the flexible wire means to extend and retract a distal end of said wire means out from and into the distal end of the tubular means;

said wire means including a flat helically twisted ribbon over its length, said ribbon having a width corresponding to the diameter of the lumen of said tubular means so as to enable longitudinal motion of the wire means while reducing relative radial motion thereof within the lumen;

said ribbon having a thickness which is thin relative to the lumen diameter such as to occupy a cross-section of generally less than that of the lumen to form a passageway for fluid to be passed through said tubular means past the wire means.

13. The surgical instrument as set forth in claim 12 wherein the length of a twist of the wire ribbon is of the order of between about four to about fifteen times the ribbon width.

14. The surgical instrument as set forth in claim 13 wherein the cross-sectional area of the ribbon is in the range from about twenty to about fifty percent of the cross-sectional area of said lumen.

15. The surgical instrument as set forth in claim 14 wherein the cross-sectional area of the ribbon is about twenty-five percent of the cross-sectional area of said lumen.

16. An instrument for use through a body orifice comprising:

an elonated flexible catheter having a lumen extending from a proximal end of the catheter to a distal end thereof along a lumen axis, the catheter having a segment which, when unrestrained, forms a bend, the bend being in a desired direction so that the catheter includes a concave outer wall portion and a convex inner wall portion, the inner wall of the catheter defining the lumen;

an opening in the catheter wall at the bend, the opening extending from the convex inner wall portion at the concave outer wall portion;

a surgical tool arranged inside the lumen having a resilient distal end portion having a bend in the desired direction, the tool having a distal tip portion, the magnitude of the bend in the end portion being selected so that the distal tip portion is arranged to be biased against the convex inner wall portion of the catheter when the tool tip portion is within the lumen;

the distal tip portion further being sized to pass into and through said opening at the bend of the catheter whereby, when the tip portion is advanced towards the bent catheter segment, it naturally extends through the opening due to its resilience and the bend in the tool end portion; and having a control wire extending from a proximal end to said distal end for control thereof, said control wire having in its cross-section separated supports located to slidingly contact the lumen wall and radially stabilize the position of the control wire within and along the catheter lumen, said supports being twisted to impart to the surgical tool a flexibility which is comparable to the flexibility of the catheter whereby the surgical tool can be manipulated with reduced longitudinal backlash.

17. A flexible, surgical instrument for use in a flexible endoscope wherein the endoscope is a duct extending from a proximal end to a distal end of the endoscope comprising:

an elongated flexible catheter sized to enter the proximal end of the endoscope duct and fit therethrough to the distal end of the endoscope duct, the catheter having a lumen surrounded by a lumen wall, the lumen extending from a proximal end of the catheter to a distal end thereof;

a surgical tool sized to slide through a lumen and through an opening in the lumen wall, the tool having a working end and a flexible control wire connected to the working end for manipulation thereof from the proximal end of the catheter, the control wire having a cross sectional area which is less than the cross section of the catheter lumen while being shaped to provide a fluid passageway between the control wire and the wall of the lumen, the control wire including means for radially stabilizing the position of the control wire in and along the catheter lumen when the control wire is placed within the lumen, said stabilizing means comprising a non-cylindrical cross-section of said wire defining at least two lateral edges comprising longitudinally extending continuous support surfaces of narrow transverse extent, the support surfaces being spaced apart from each other a desired amount so that said support surfaces slidingly contact the lumen wall, and the control wire having structural rigidity and integrity along its length to insure accurate manipulation of a tip portion of the working end of the surgical tool back and forth throuhgh an opening in the lumen, whereby the working end of the surgical toool can be manipulated with reduced longitudinal backlash for an enhancement in the accuracy of the control over the position of the working end of the tool and wherein the control wire is in the form of a longitudinal flexible central wire having a plurality of at least three longitudinal ribs which radially extend from the central wirre to slidingly contact the lumen wall.

18. The flexible surgical insturment as set forth in claim 17 wherein the control wire is in the form of an elongated rectangular ribbon having said lateral edges and having a width sized to enable said support surfaces to slidingly contact the lumen wall, said ribbon being helically twisted to maintain the ribbon radially stabilized within the catheter lumen throughout flectures of the endoscope and provide a continuous fluid passageway.

19. An instrument for use in a flexible endoscope by insertion into a channel surrounded by a channel wall, comprising:

a surgical tool having a distal working end and a flexible longitudinal control wire connected to the distal workking end for the manipulation thereof;

the control wire having a cross-sectional area which is less than the cross-sectional area of the channels through which the surgical tool is to be inserted, the cross section being further selectively shaped to enable formation of a fluid passageway eternal of the control wire upon inserting into the channel, the control wire including means for radially stabilizing the position of the control wire in and along the channel when the control wire is placed within the channel, said stabilizing means comprising a non-cylindrical cross-section of said wire defining at least two lateral edges comprising longitudinally extending continous support surfaces of narrow transverse extend, the support surfaces being spaced aprt from each other a desired amount so that the support surfaces slidingly contact the channel wall and the control wire having structural rigidity and integrity along its length to assure accurate extension and retraction of the working end of the tool relative to the channel wall, whereby the tool, when placed within the channel, may be moved therealong substantially without backlash for improved positional control over the distal working end of the insturment from the proximal end of the endoscope and said control wire being formed of a longitudinal ribbon of generally rectangular cross section with sides to form said at least two lateral edges, said longitudinal ribbon first being provided along its length with a plurality of twists to form a sprial control wire capable of being flexed in various planes while maintaining said radial positional stability within the channel when the instrument is longitudinally moved within the channel.

* * * * *